(12) United States Patent
Nad et al.

(10) Patent No.: US 12,728,088 B2
(45) Date of Patent: Sep. 8, 2026

(54) FREE STANDING FILM

(71) Applicant: Dow Silicones Corporation, Midland, MI (US)

(72) Inventors: Saugata Nad, Brussels (BE); Serge Creutz, Liege (BE); Christel Simon, Lobbes (BE)

(73) Assignee: Dow Silicones Corporation, Midland, MI (US)

( * ) Notice: Subject to any disclaimer, the term of this patent is extended or adjusted under 35 U.S.C. 154(b) by 44 days.

(21) Appl. No.: 18/836,049

(22) PCT Filed: Feb. 10, 2023

(86) PCT No.: PCT/US2023/012752
§ 371 (c)(1),
(2) Date: Aug. 6, 2024

(87) PCT Pub. No.: WO2023/158590
PCT Pub. Date: Aug. 24, 2023

(65) Prior Publication Data

US 2025/0032393 A1 Jan. 30, 2025

Related U.S. Application Data

(60) Provisional application No. 63/310,668, filed on Feb. 16, 2022.

(51) Int. Cl.

| | |
|---|---|
| ***A61K 8/81*** | (2006.01) |
| ***A61K 8/04*** | (2006.01) |
| ***A61K 8/44*** | (2006.01) |
| ***A61K 8/73*** | (2006.01) |
| ***A61Q 5/06*** | (2006.01) |

(52) U.S. Cl.
CPC ............ *A61K 8/8147* (2013.01); *A61K 8/042* (2013.01); *A61K 8/44* (2013.01); *A61K 8/732* (2013.01); *A61Q 5/06* (2013.01); *A61K 2800/262* (2013.01); *A61K 2800/48* (2013.01)

(58) Field of Classification Search
CPC ........ A61K 8/8147; A61K 8/042; A61K 8/44; A61K 8/732; A61K 2800/262; A61K 2800/48; A61Q 5/06
See application file for complete search history.

(56) References Cited

U.S. PATENT DOCUMENTS

| | | | |
|---|---|---|---|
| 7,022,656 | B2 | 4/2006 | Verrall et al. |
| 10,982,175 | B2 | 4/2021 | Karikari et al. |
| 11,168,289 | B2 | 11/2021 | Friedrich et al. |

FOREIGN PATENT DOCUMENTS

| | | | | |
|---|---|---|---|---|
| WO | WO2020/223037 | * | 5/2021 | ............. C04B 24/38 |
| WO | 2022026349 | | 2/2022 | |
| WO | 2022182616 | | 9/2022 | |

* cited by examiner

*Primary Examiner* — Trevor Love
(74) *Attorney, Agent, or Firm* — Thomas S. Deibert

(57) ABSTRACT

A free standing film is provide, including: 20 to 100 wt %, based on weight of the free standing film, of an irreversibly crosslinked cellulose ether containing 0.1 to 0.6 wt %, based on weight of the crosslinked cellulose ether, of polyether groups. Unit dose packages including the free standing film are also provided.

10 Claims, No Drawings

FREE STANDING FILM

The present invention relates to a free standing film. In particular, the present invention relates to a free standing film comprising 20 to 100 wt %, based on weight of the free standing film, of a crosslinked cellulose ether containing 0.1 to 0.6 wt %, based on weight of the crosslinked cellulose ether, of polyether groups; and to unit dose detergent packages made with the free standing film.

Conventional water-soluble polymeric films have found use as packaging materials that facilitate the simplification of dispersing, pouring, dissolving and dosing of materials to be delivered. For example, packages prepared from conventional water-soluble films are commonly used to contain a premeasured unit dose of a household care composition, such as, a hard surface cleaners, dish detergents and laundry detergent formulations. Because these household care compositions are generally effective in solution with water, it is possible to provide a concentrate that can be mixed with water to form the cleaning solution. The concentrate may be packaged and shipped separately from the majority of the water used to make the cleaning solution. The end user may then form the cleaning solution from water and the concentrate.

An issue with the concentrates is that they benefit from precise mixing to ensure proper concentration of actives in the household care composition formed. Too dilute of a solution may result in poor cleaning performance. Too concentrated a solution may result in residue remaining on the cleaned surface. In addition, too concentrated of a cleaning solution may constitute a waste of the cleaning concentrate.

To alleviate concerns with improper dilution of the cleaning concentrate, it has been found beneficial to package single use, pre-measured amounts of cleaning concentrate in individual packages. A premeasured amount of cleaning concentrate is preferably added to a specific volume of water to form a properly concentrated cleaning solution. It is further possible to package the concentrate with a properly sized container such that the user simply adds the cleaning concentrate to the container and fills the remainder of the container with water. When the container is empty, a replacement package of concentrate may be added to the container, and the remainder once again filled with water.

It has also been found useful to package cleaning concentrates in water soluble packaging, particularly in single use, premeasured amounts. Forming the cleaning solution is made easier by the use of water soluble packaging containing the concentrate because the user may simply add the water soluble package to a container and then add the correct amount of water to form the desired cleaning solution. As the water soluble packaging dissolves, the cleaner is released and forms a cleaning solution having the proper concentration of cleaner.

One problem with conventionally packaged concentrates in water soluble packaging is that the cleaning formulations formed therewith have inadequate viscosity given the difficulty of stably formulating conventional rheology modifiers into the concentrated cleaner incorporated into the package. The lack of viscosity in the cleaning composition formed from the packaged concentrate can be negatively viewed by consumers, in for example, hand dish washing formulations and can detrimentally impede performance in hard surface cleaners where rheology can be required, for example, vertical cling for cleaning bathroom tiles.

Accordingly, there remains a continuing need for a unit dose detergent package for preparing a household care composition, wherein the household care composition formed has enhanced viscosity. In particular, there remains a need for free standing film compositions that are capable of imparting thickening benefits to household care compositions formed by unit dose detergent package made with such free standing film compositions.

The present invention provides a free standing film, comprising: 20 to 100 wt %, based on weight of the free standing film, of a crosslinked cellulose ether containing 0.1 to 0.6 wt %, based on weight of the crosslinked cellulose ether, of polyether groups.

The present invention provides a free standing film, comprising: 20 to 100 wt %, based on weight of the free standing film, of a crosslinked cellulose ether containing 0.1 to 0.6 wt %, based on weight of the crosslinked cellulose ether, of polyether groups; wherein the crosslinked cellulose ether is an irreversibly crosslinked cellulose ether.

The present invention provides a free standing film, comprising: 20 to 100 wt %, based on weight of the free standing film, of a crosslinked cellulose ether containing 0.1 to 0.6 wt %, based on weight of the crosslinked cellulose ether, of polyether groups; wherein the free standing film has an average thickness of 5 to 200 μm.

The present invention provides a free standing film, comprising: 20 to 100 wt %, based on weight of the free standing film, of a crosslinked cellulose ether containing 0.1 to 0.6 wt %, based on weight of the crosslinked cellulose ether, of polyether groups; and at least one of: (a) 5 to 80 wt %, based on weight of the free standing film, of a partially hydrolyzed poly(vinyl acetate); (b) 0.1 to 45 wt %, based on weight of the free standing film, of a crosslinking agent; (c) 0.1 to 45 wt %, based on weight of the free standing film, of a poly(ethylene oxide) having a weight average molecular weight of 20,000 to 2,000,000 Daltons; (d) 0.1 to 35 wt %, based on weight of the free standing film, of a poly(alkylene glycol) having a weight average molecular weight of >400 to 5,300 Daltons; (e) 0.1 to 45 wt %, based on weight of the free standing film, of a plasticizer; (f) 0.1 to 10 wt %, based on weight of the free standing film, of a poly(isobutylene-co-maleic anhydride) copolymer, wherein the poly(isobutylene-co-maleic anhydride) copolymer is at least partially neutralized; and (g) 0.01 to 1.8 wt %, based on weight of the free standing film, of a poly(vinyl pyrrolidone).

The present invention provides a unit dose detergent package, comprising: a free standing film of the present invention; and a detergent formulation, comprising 10 to 60 wt %, based on weight of the detergent formulation, of a surfactant; wherein the free standing film forms a cavity; wherein the detergent formulation is disposed within the cavity; wherein the detergent formulation is in contact with the free standing film; and wherein the free standing film encapsulates the detergent formulation.

DETAILED DESCRIPTION

We have found a unique free standing film that facilitates significant thickening of end use detergent formulations formed using a unit dose package comprising same.

Unless otherwise indicated, ratios, percentages, parts, and the like are by weight.

As used herein, unless otherwise indicated, the phrase "molecular weight" or Mw refers to the weight average molecular weight as measured in a conventional manner with gel permeation chromatography (GPC) and polyacrylic acid standards. GPC techniques are discussed in detail in Modem Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p. 81-84. Molecular weights are reported herein in units of Daltons.

The term "DS" as used herein and in the appended claims means the number of alkyl substituted OH groups per anhydroglucose unit in a cellulose ether, as determined by the Zeisel Method.

The term "DS (methyl)" or "DS (M)" as used herein and in the appended claims means the number of methyl substituted OH groups per anhydroglucose unit in a cellulose ether, as determined by the Zeisel Method.

The term "MS" as used herein and in the appended claims means the number of moles of etherification reagent which are bound as ether per mol of anhydroglucose unit as hydroxyalkyl substituents in a cellulose ether, as determined by the Zeisel Method.

The term "MS (hydroxyethyl)" or "MS (HE)" as used herein and in the appended claims means the number of moles of etherification reagent which are bound as ether per mol of anhydroglucose unit as hydroxyethyl substituents in a cellulose ether, as determined by the Zeisel Method.

The term "MS (hydroxypropyl)" or "MS (HP)" as used herein and in the appended claims means the number of moles of etherification reagent which are bound as ether per mol of anhydroglucose unit as hydroxypropyl substituents in a cellulose ether, as determined by the Zeisel Method.

The term "Zeisel Method" refers to the Zeisel cleavage procedure for determination of MS and DS. See G. Bartelmus and R. Ketterer, *Zeitschrift fuer Analytische Chemie*, Vol. 286 (1977, Springer, Berline, DE), pages 161-190.

Preferably, the free standing film of the present invention, comprises: 20 to 100 wt % (preferably, at least 25 wt %; more preferably, at least 40 wt %; most preferably, at least 60 wt %) (preferably, no more than 98 wt %; more preferably, no more than 95 wt %; most preferably, no more than 90 wt %), based on weight of the free standing film, of a crosslinked cellulose ether containing 0.1 to 0.6 wt %, based on weight of the crosslinked cellulose ether, of polyether groups (preferably, wherein the crosslinked cellulose ether is an irreversibly crosslinked cellulose ether).

Preferably, the free standing film of the present invention has an average thickness of 5 to 200 μm (preferably, 20 to 100 μm; more preferably, 35 to 100 μm; most preferably, 40 to 85 μm).

Preferably, the free standing films of the present invention have a disintegration time of less than 90 seconds as determined at 40° C. using distilled water according to MS™ 205.

Preferably, the free standing film of the present invention is water soluble. The term "water soluble" as used herein in reference to a free standing film of the present invention means that a sample of the free standing film (0.5"×1.5"×76 μm) when placed in 20 mL of tap water having a temperature of 5 to 25° C. in a sample vial; left to sit undisturbed for two (2) minutes; then shaken for sixty (60) seconds and then filtered through a 0.025 mm mesh screen, wherein only a slight haze is perceptible and no residue or grit is observed according to the procedure set forth herein in the Examples.

Preferably, the free standing films of the present invention are water soluble based on film solubility tests conducted according to MS™ (MonoSol Standard Test Method) 205 in distilled water at 25° C.

Preferably, the free standing film of the present invention, comprises: 20 to 100 wt % (preferably, at least 25 wt %; more preferably, at least 40 wt %; most preferably, at least 60 wt %) (preferably, no more than 98 wt %; more preferably, no more than 95 wt %; most preferably, no more than 90 wt %), based on weight of the free standing film, of a crosslinked cellulose ether containing 0.1 to 0.6 wt %, based on weight of the crosslinked cellulose ether, of polyether groups; wherein the crosslinked cellulose ether comprises a base cellulose ether and crosslinks; wherein the crosslinks contain the polyether groups and wherein the base cellulose ether is a mixed cellulose ether containing hydroxyalkyl ether groups and alkyl ether groups. More preferably, the free standing film of the present invention, comprises: 20 to 100 wt % (preferably, at least 25 wt %; more preferably, at least 40 wt %; most preferably, at least 60 wt %) (preferably, no more than 98 wt %; more preferably, no more than 95 wt %; most preferably, no more than 90 wt %), based on weight of the free standing film, of a crosslinked cellulose ether containing 0.1 to 0.6 wt %, based on weight of the crosslinked cellulose ether, of polyether groups; wherein the crosslinked cellulose ether comprises a base cellulose ether and crosslinks; wherein the crosslinks contain the polyether groups and wherein the base cellulose ether is selected from the group consisting of hydroxyethyl methylcellulose, hydroxypropyl methyl cellulose, methyl hydroxyethyl hydroxypropylcellulose, ethyl hydroxyethyl cellulose and combinations thereof. Most preferably, the free standing film of the present invention, comprises: 20 to 100 wt % (preferably, at least 25 wt %; more preferably, at least 40 wt %; most preferably, at least 60 wt %) (preferably, no more than 98 wt %; more preferably, no more than 95 wt %; most preferably, no more than 90 wt %), based on weight of the free standing film, of a crosslinked cellulose ether containing 0.1 to 0.6 wt %, based on weight of the crosslinked cellulose ether, of polyether groups; wherein the crosslinked cellulose ether comprises a base cellulose ether and crosslinks; wherein the crosslinks contain the polyether groups and wherein the base cellulose ether is hydroxyethyl methylcellulose.

Preferably, the free standing film of the present invention, comprises: 20 to 100 wt % (preferably, at least 25 wt %; more preferably, at least 40 wt %; most preferably, at least 60 wt %) (preferably, no more than 98 wt %; more preferably, no more than 95 wt %; most preferably, no more than 90 wt %), based on weight of the free standing film, of a crosslinked cellulose ether containing 0.1 to 0.6 wt %, based on weight of the crosslinked cellulose ether, of polyether groups; wherein the crosslinked cellulose either is an irreversibly crosslinked cellulose ether. More preferably, the free standing film of the present invention, comprises: 20 to 100 wt % (preferably, at least 25 wt %; more preferably, at least 40 wt %; most preferably, at least 60 wt %) (preferably, no more than 98 wt %; more preferably, no more than 95 wt %; most preferably, no more than 90 wt %), based on weight of the free standing film, of a crosslinked cellulose ether containing 0.1 to 0.6 wt %, based on weight of the crosslinked cellulose ether, of polyether groups; wherein the crosslinked cellulose ether comprises a base cellulose ether and crosslinks; wherein the crosslinks contain the polyether groups; wherein the base cellulose ether is a mixed cellulose ether containing hydroxyalkyl ether groups and alkyl ether groups and wherein the crosslinked cellulose either is an irreversibly crosslinked cellulose ether. Still more preferably, the free standing film of the present invention, comprises: 20 to 100 wt % (preferably, at least 25 wt %; more preferably, at least 40 wt %; most preferably, at least 60 wt %) (preferably, no more than 98 wt %; more preferably, no more than 95 wt %; most preferably, no more than 90 wt %), based on weight of the free standing film, of a crosslinked cellulose ether containing 0.1 to 0.6 wt %, based on weight of the crosslinked cellulose ether, of polyether groups;

wherein the crosslinked cellulose ether comprises a base cellulose ether and crosslinks; wherein the crosslinks contain the polyether groups; wherein the base cellulose ether is selected from the group consisting of hydroxyethyl methylcellulose, hydroxypropyl methyl cellulose, methyl hydroxyethyl hydroxypropylcellulose, ethyl hydroxyethyl cellulose and combinations thereof and wherein the crosslinked cellulose either is an irreversibly crosslinked cellulose ether. Most preferably, the free standing film of the present invention, comprises: 20 to 100 wt % (preferably, at least 25 wt %; more preferably, at least 40 wt %; most preferably, at least 60 wt %) (preferably, no more than 98 wt %; more preferably, no more than 95 wt %; most preferably, no more than 90 wt %), based on weight of the free standing film, of a crosslinked cellulose ether containing 0.1 to 0.6 wt %, based on weight of the crosslinked cellulose ether, of polyether groups; wherein the crosslinked cellulose ether comprises a base cellulose ether and crosslinks; wherein the crosslinks contain the polyether groups; wherein the base cellulose ether is hydroxyethyl methylcellulose and wherein the crosslinked cellulose either is an irreversibly crosslinked cellulose ether.

Preferably, the crosslinked cellulose ether contains 0.1 to 0.6 wt % (preferably, 0.12 to 0.6 wt %; more preferably, 0.12 to 0.45 wt %; most preferably, 0.12 to 0.29 wt %), based on weight of the crosslinked cellulose ether, of polyether groups. More preferably, the crosslinked cellulose ether contains 0.1 to 0.6 wt % (preferably, 0.12 to 0.6 wt %; more preferably, 0.12 to 0.45 wt %; most preferably, 0.12 to 0.29 wt %), based on weight of the crosslinked cellulose ether, of polyether groups; wherein the polyether groups are polyoxyalkylene groups having 2 to 100 (preferably, 2 to 20; more preferably, 3 to 15) oxyalkylene groups per crosslink. Most preferably, the crosslinked cellulose ether contains 0.1 to 0.6 wt % (preferably, 0.12 to 0.6 wt %; more preferably, 0.12 to 0.45 wt %; most preferably, 0.12 to 0.29 wt %), based on weight of the crosslinked cellulose ether, of polyether groups; wherein the polyether groups are polyoxypropylene groups having 2 to 100 (preferably, 2 to 20; more preferably, 3 to 15) oxypropylene groups per crosslink.

Preferably, crosslinked cellulose ether comprises a base cellulose ether having crosslinks containing 0.1 to 0.6 wt %, based on weight of the crosslinked cellulose ether, of polyether groups. Preferably, the base cellulose ether is selected from hydroxyalkyl cellulose ethers, alkyl cellulose ethers and combinations thereof. Examples of base cellulose ethers include, for example, methylcellulose, ethylcellulose, propylcellulose, butylcellulose, hydroxyethyl methylcellulose, hydroxypropyl methylcellulose, hydroxyethylcellulose, ethylhydroxyethylcellulose, methylethylhydroxyethylcellulose, hydrophobically modified ethylhydroxyethylcellulose, hydrophobically modified hydroxyethylcellulose, sulfoethyl methylhydroxyethylcellulose, sulfoethyl methylhydroxypropylcellulose and sulfoethyl hydroxyethylcellulose. Preferably, the base cellulose ethers are mixed cellulose ethers that contain both hydroxyalkyl ether groups and alkyl ether groups, such as, alkyl hydroxyethyl cellulose and hydroxyalkyl methylcellulose (e.g., hydroxyethyl methylcellulose, hydroxypropyl methylcellulose, methyl hydroxyethyl hydroxypropylcellulose and ethylhydroxyethyl cellulose).

Preferably, the base cellulose ether contains hydroxyalkyl ether substitutions. More preferably, the base cellulose ether has a degree of hydroxyethyl ether substitutions, MS (HE), or hydroxypropyl ether substitutions, MS (HP), of 1.5 to 4.5 (preferably, 2.0 to 3.0).

Preferably, the base cellulose ether contains methyl ether substitutions. More preferably, the base cellulose ether has a degree of methyl ether substitution, DS (M), of 1.2 to 2.1 (preferably, 1.3 to 1.7; more preferably, 1.35 to 1.60).

Preferably, the base cellulose ether is a mixed cellulose ether containing hydroxyalkyl ether substitutions and alkyl ether substitutions. More preferably, the base cellulose ether is a mixed cellulose ether having a degree of hydroxyethyl ether substitution, MS (HE), of 0.05 to 0.75 (preferably, 0.15 to 0.45; more preferably, 0.20 to 0.40) and a degree of methyl ether substitution, DS (M), of 1.2 to 2.1 (preferably, 1.3 to 1.7, more preferably, 1.35 to 1.60).

Preferably, the base cellulose ether is a mixed cellulose ether containing hydroxyalkyl ether substitutions and alkyl ether substitutions. More preferably, the base cellulose ether is a mixed cellulose ether having a degree of hydroxypropyl ether substitution, MS (HP), of 0.1 to 1.5 (preferably, 0.2 to 1.2) and a degree of methyl ether substitution, DS (M), of 1.2 to 2.1 (preferably, 1.3 to 2.0).

Preferably, the crosslinked cellulose ether comprises a base cellulose ether having crosslinks containing 0.1 to 0.6 wt %, based on weight of the crosslinked cellulose ether, of polyether groups; wherein the base cellulose ether is a hydroxyethyl methyl cellulose and wherein the crosslinks are polyoxypropylene dioxyethylene ether crosslinks, such as those produced as the reaction product of hydroxyethyl methyl cellulose with polypropylene glycol (PPG) glycidylether.

Crosslinking agents used to crosslink the base cellulose ether to form the crosslinked cellulose ether include compounds having a polyoxyalkylene or poly(alkylene glycol) group and two or more (preferably, two) crosslinking groups, such as, halogen groups, glycidyl or epoxy groups, and ethylenically unsaturated groups (e.g., vinyl groups) that form ether bonds with the base cellulose ether to form the crosslinked cellulose ether. Preferably, the crosslinking agent is selected from the group consisting of 1,2-dichloro (poly)alkoxy ethers, dichloropolyoxyethylene, diglycidyl polyalkoxy ethers, diglycidyl phosphonate, divinyl polyoxyalkylenes containing a sulphone group. Crosslinking agents having two different types of functional groups can be used. Examples include diglycidyl polyoxypropylenes and glycidyl(poly)oxyalkyl methacrylate. Preferably, the crosslinking agent contains 2 to 100 (preferably, 2 to 20; more preferably, 3 to 15) oxyalkylene groups per molecule.

Preferably, the amount of crosslinking agent included in the crosslinked cellulose ether ranges from 0.0001 to 0.05 eq (preferably, 0.0005 to 0.01 eq; more preferably, 0.001 to 0.005 eq), wherein the unity "eq" represents the molar ratio of moles of the crosslinking agent relative to the number of moles of anhydroglucose units (AGU) in the base cellulose ether.

Preferably, the crosslinked cellulose ether is an irreversibly crosslinked cellulose ether. That is, the crosslinks in the crosslinked cellulose ether do not break down during the intended use of the crosslinked cellulose ether under normal conditions. In contrast, reversible crosslinks will break down during the intended use of the crosslinked cellulose ether under normal conditions. An example of reversible crosslinks in cellulose ethers intended for use in laundry detergent formulations are those created using aldehyde based crosslinkers (e.g., glyoxal), which crosslinks break down upon dissolution of the crosslinked material in water.

Preferably, the free standing film of the present invention further comprises at least one of (a) 5 to 80 wt % (preferably, 5 to 75 wt %; more preferably, 7.5 to 60 wt %; most preferably, 10 to 40 wt %), based on weight of the free standing film, of a partially hydrolyzed poly(vinyl acetate) (preferably, wherein the partially hydrolyzed poly(vinyl acetate) is 75 to 99% hydrolyzed (more preferably, 80 to 99% hydrolyzed; most preferably, 90 to 99% hydrolyzed)); (b) 0.1 to 45 wt % (preferably, 10 to 40 wt %; more preferably, 15 to 40 wt %; most preferably, 20 to 35 wt %), based on weight of the free standing film, of a crosslinking agent; (c) 0.1 to 45 wt % (preferably, 1 to 40 wt %; more preferably, 5 to 25 wt %; most preferably, 10 to 15 wt %), based on weight of the free standing film, of a poly(ethylene oxide) having a weight average molecular weight of 20,000 to 2,000,000 Daltons (preferably, 100,000 to 1,000,000 Daltons; more preferably, 250,000 to 750,000 Daltons; most preferably, 350,000 to 650,000 Daltons); (d) 0.1 to 35 wt % (preferably, 1 to 25 wt %; more preferably, 2 to 15 wt %; most preferably, 4 to 7.5 wt %), based on weight of the free standing film, of a poly(alkylene glycol) having a weight average molecular weight of >400 to 5,300 Daltons (preferably, 500 to 1,500 Daltons; more preferably, 750 to 1,200 Daltons; most preferably, 800 to 1,000 Daltons); (e) 0.1 to 45 wt % (preferably, 1 to 40 wt %; more preferably, 2 to 35 wt %; most preferably, 5 to 25 wt %), based on weight of the free standing film, of a plasticizer; (f) 0.1 to 10 wt % (preferably, 0.5 to 7.5 wt %; more preferably, 1 to 6 wt %; most preferably, 2 to 5.5 wt %), based on weight of the free standing film, of a poly(isobutylene-co-maleic anhydride) copolymer, wherein the poly(isobutylene-co-maleic anhydride) copolymer is at least partially neutralized (preferably, wherein the degree of neutralization is 50 to 100%; more preferably, 75 to 100%; most preferably, 95 to 100%); and (g) 0.01 to 1.8 wt %, based on weight of the free standing film, of a poly(vinyl pyrrolidone) (preferably, wherein the poly(vinyl pyrrolidone) has a weight average molecular weight of 5,000 to 2,000,000 Daltons (preferably, 10,000 to 1,500,000 Daltons; more preferably, 20,000 to 100,000 Daltons; most preferably, 20,000 to 50,000 Daltons) (preferably, wherein the weight ratio of the partially hydrolyzed poly(vinyl acetate) to the poly(vinyl pyrrolidone) in the free standing film is >10:1 (preferably, at least 100:1; more preferably, at least 150:1; most preferably, 150:1 to 600:1).

Preferably, the free standing film of the present invention comprises: 20 to 95 wt % (preferably, at least 25 wt %; more preferably, at least 40 wt %; most preferably, at least 60 wt %) (preferably, no more than 90 wt %), based on weight of the free standing film, of a crosslinked cellulose ether containing 0.1 to 0.6 wt %, based on weight of the crosslinked cellulose ether, of polyether groups; and 5 to 80 wt % (preferably, at least 5 wt %; more preferably, at least 10 wt %) (preferably, no more than 75 wt %; more preferably, no more than 60 wt %; most preferably, no more than 40 wt %), based on weight of the free standing film, of a partially hydrolyzed poly(vinyl acetate) (preferably, 75 to 99% hydrolyzed; more preferably, 80 to 99% hydrolyzed; most preferably, 90 to 99% hydrolyzed).

Preferably, the free standing film of the present invention, further comprises: 5 to 80 wt % (preferably, 5 to 75 wt %; more preferably, 7.5 to 60 wt %; most preferably, 10 to 40 wt %) (preferably, at least 5 wt %; more preferably, at least 10 wt %) (preferably, no more than 75 wt %; more preferably, no more than 60 wt %; most preferably, no more than 40 wt %), based on weight of the free standing film, of a partially hydrolyzed poly(vinyl acetate) (preferably, wherein the partially hydrolyzed poly(vinyl acetate) is 75 to 99% hydrolyzed (more preferably, 80 to 99% hydrolyzed; most preferably, 90 to 99% hydrolyzed)). More preferably, the free standing film of the present invention, further comprises: 5 to 80 wt % (preferably, 5 to 75 wt %; more preferably, 7.5 to 60 wt %; most preferably, 10 to 40 wt %) (preferably, at least 5 wt %; more preferably, at least 10 wt %) (preferably, no more than 75 wt %; more preferably, no more than 60 wt %; most preferably, no more than 40 wt %), based on weight of the free standing film, of a partially hydrolyzed poly(vinyl acetate); wherein the partially hydrolyzed poly(vinyl acetate) has a weight average molecular weight of 10,000 to 250,000 Daltons (preferably, 20,000 to 175,000 Daltons; more preferably, 30,000 to 100,000 Daltons; most preferably, 55,000 to 80,000 Daltons) (preferably, wherein the partially hydrolyzed poly(vinyl acetate) is 75 to 99% hydrolyzed (more preferably, 80 to 99% hydrolyzed; most preferably, 90 to 99% hydrolyzed)).

Preferably, the free standing film of the present invention, further comprises 0.1 to 45 wt % (preferably, 10 to 40 wt %; more preferably, 15 to 40 wt %; most preferably, 20 to 35 wt %), based on weight of the free standing film, of a crosslinking agent. More preferably, the free standing film of the present invention, further comprises 0.1 to 45 wt % (preferably, 10 to 40 wt %; more preferably, 15 to 40 wt %; most preferably, 20 to 35 wt %), based on weight of the free standing film, of a crosslinking agent; wherein the crosslinking agent is an ionic crosslinking agent (e.g., alkali metal salts, alkaline metal salts and mixtures thereof). Preferably, the crosslinking agent is selected from ionic crosslinking agents including $Ca^{2+}$, $Mg^{2+}$, $Al^{2+}$, $Al^{3+}$, $Zn^{2+}$ and mixtures thereof. More preferably, the crosslinking agent is selected from ionic crosslinking agents including $Ca^{2+}$, $Zn^{2+}$ and mixtures thereof. Preferably, the cations are provided as a water soluble inorganic salt or complex, for example, $CaCl_2$), ZnO, Zinc ammonium bicarbonate.

Preferably, the free standing film of the present invention, further comprises 0.1 to 45 wt % (preferably, 1 to 40 wt %; more preferably, 5 to 25 wt %; most preferably, 10 to 15 wt %), based on weight of the free standing film, of a poly (ethylene oxide). More preferably, the free standing film of the present invention, further comprises 0.1 to 45 wt % (preferably, 1 to 40 wt %; more preferably, 5 to 25 wt %; most preferably, 10 to 15 wt %), based on weight of the free standing film, of a poly(ethylene oxide); wherein the poly (ethylene oxide) has a weight average molecular weight of 20,000 to 2,000,000 Daltons (preferably, 100,000 to 1,000,000 Daltons; more preferably, 250,000 to 750,000 Daltons; most preferably, 350,000 to 650,000 Daltons).

Preferably, the free standing film of the present invention further comprises 0.1 to 35 wt % (preferably, 1 to 25 wt %; more preferably, 2 to 15 wt %; most preferably, 4 to 7.5 wt %), based on weight of the free standing film, of a poly (alkylene glycol). More preferably, the free standing film of the present invention further comprises 0.1 to 35 wt % (preferably, 1 to 25 wt %; more preferably, 2 to 15 wt %; most preferably, 4 to 7.5 wt %), based on weight of the free standing film, of a poly(alkylene glycol); wherein the poly (alkylene glycol) has a weight average molecular weight of >400 to 5,300 Daltons (preferably, 500 to 1,500 Daltons; more preferably, 750 to 1,200 Daltons; most preferably, 800 to 1,000 Daltons). Most preferably, the free standing film of the present invention further comprises 0.1 to 35 wt % (preferably, 1 to 25 wt %; more preferably, 2 to 15 wt %; most preferably, 4 to 7.5 wt %), based on weight of the free standing film, of a poly(alkylene glycol); wherein the poly (alkylene glycol) has a weight average molecular weight of >400 to 5,300 Daltons (preferably, 500 to 1,500 Daltons; more preferably, 750 to 1,200 Daltons; most preferably, 800 to 1,000 Daltons) and wherein the poly(alkylene glycol) is a random copolymer of ethylene oxide and propylene oxide.

Preferably, the free standing film of the present invention, further comprises 0.1 to 45 wt % (preferably, 1 to 40 wt %; more preferably, 2 to 35 wt %; most preferably, 5 to 25 wt %), based on weight of the free standing film, of a plasticizer. More preferably, the free standing film of the present invention, further comprises 0.1 to 45 wt % (preferably, 1 to 40 wt %; more preferably, 2 to 35 wt %; most preferably, 5 to 25 wt %), based on weight of the free standing film, of a plasticizer; wherein the plasticizer is selected from the group consisting of dipropylene glycol, isomalt, maltitol, sorbitol, xylitol, erythritol, adonitol, dulcitol, pentaerythritol, mannitol, glycerin, diglycerin, ethylene glycol, diethylene glycol, triethyleneglycol, tetraethylene glycol, polyethylene glycol having a weight average molecular weight of up to 400 Daltons, neopentyl glycol, propylene glycol, 2-methyl-1,3-propanediol, trimethylolpropane, polyether polyols having a weight average molecular weight of up to 400 Daltons, and mixtures thereof. Still more preferably, the free standing film of the present invention, further comprises 0.1 to 45 wt % (preferably, 1 to 40 wt %; more preferably, 2 to 35 wt %; most preferably, 5 to 25 wt %), based on weight of the free standing film, of a plasticizer; wherein the plasticizer is selected from the group consisting of dipropylene glycol, sorbitol, glycerin and mixtures thereof. Most preferably, the free standing film of the present invention, further comprises 0.1 to 45 wt % (preferably, 1 to 40 wt %; more preferably, 2 to 35 wt %; most preferably, 5 to 25 wt %), based on weight of the free standing film, of a plasticizer; wherein the plasticizer includes a mixture of dipropylene glycol, sorbitol and glycerin.

Preferably, the free standing film of the present invention, further comprises 0.1 to 10 wt % (preferably, 0.5 to 7.5 wt %; more preferably, 1 to 6 wt %; most preferably, 2 to 5.5 wt %), based on weight of the free standing film, of a poly(isobutylene-co-maleic anhydride) copolymer. More preferably, the free standing film of the present invention, further comprises 0.1 to 10 wt % (preferably, 0.5 to 7.5 wt %; more preferably, 1 to 6 wt %; most preferably, 2 to 5.5 wt %), based on weight of the free standing film, of a poly(isobutylene-co-maleic anhydride) copolymer; wherein the poly(isobutylene-co-maleic anhydride) copolymer is at least partially neutralized (preferably, wherein the degree of neutralization is 50 to 100%; more preferably, 75 to 100%; most preferably, 95 to 100%). Most preferably, the free standing film of the present invention, further comprises 0.1 to 10 wt % (preferably, 0.5 to 7.5 wt %; more preferably, 1 to 6 wt %; most preferably, 2 to 5.5 wt %), based on weight of the free standing film, of a poly(isobutylene-co-maleic anhydride) copolymer; wherein the poly(isobutylene-co-maleic anhydride) copolymer is at least partially neutralized (preferably, wherein the degree of neutralization is 50 to 100%; more preferably, 75 to 100%; most preferably, 95 to 100%) and wherein the poly(isobutylene-co-maleic anhydride) copolymer has a weight average molecular weight of 50,000 to 500,000 Daltons (preferably, 75,000 to 250,000 Daltons; more preferably, 100,000 to 200,000 Daltons; most preferably, 140,000 to 180,000 Daltons).

Preferably, the free standing film of the present invention, further comprises 0.1 to 10 wt % (preferably, 0.5 to 7.5 wt %; more preferably, 1 to 6 wt %; most preferably, 2 to 5.5 wt %), based on weight of the free standing film, of a poly(isobutylene-co-maleic anhydride) copolymer; wherein the poly(isobutylene-co-maleic anhydride) copolymer is at least partially neutralized with at least one of an alkali earth metal hydroxide, an alkaline earth metal hydroxide and an ionomer, wherein the degree of neutralization is 50 to 100% (more preferably, 75 to 100%; most preferably, 95 to 100%). More preferably, the free standing film of the present invention, further comprises 0.1 to 10 wt % (preferably, 0.5 to 7.5 wt %; more preferably, 1 to 6 wt %; most preferably, 2 to 5.5 wt %), based on weight of the free standing film, of a poly(isobutylene-co-maleic anhydride) copolymer; wherein the poly(isobutylene-co-maleic anhydride) copolymer is at least partially neutralized with at least one of an alkali earth metal hydroxide and an alkaline earth metal hydroxide, wherein the degree of neutralization is 50 to 100% (more preferably, 75 to 100%; most preferably, 95 to 100%). Most preferably, the free standing film of the present invention, further comprises 0.1 to 10 wt % (preferably, 0.5 to 7.5 wt %; more preferably, 1 to 6 wt %; most preferably, 2 to 5.5 wt %), based on weight of the free standing film, of a poly(isobutylene-co-maleic anhydride) copolymer; wherein the poly(isobutylene-co-maleic anhydride) copolymer is at least partially neutralized with at least one of sodium hydroxide, potasium hydroxide, magnesium hydroxide and calcium hydroxide, wherein the degree of neutralization is 50 to 100% (more preferably, 75 to 100%; most preferably, 95 to 100%).

Preferably, the free standing film of the present invention, further comprises 0.01 to 1.8 wt %, based on weight of the free standing film, of a poly(vinyl pyrrolidone). More preferably, the free standing film of the present invention, further comprises 0.01 to 1.8 wt %, based on weight of the free standing film, of a poly(vinyl pyrrolidone); wherein the poly(vinyl pyrrolidone) has a weight average molecular weight of 5,000 to 2,000,000 Daltons (preferably, 10,000 to 1,500,000 Daltons; more preferably, 20,000 to 100,000 Daltons; most preferably, 20,000 to 50,000 Daltons). Most preferably, the free standing film of the present invention, further comprises 0.01 to 1.8 wt %, based on weight of the free standing film, of a poly(vinyl pyrrolidone); wherein the poly(vinyl pyrrolidone) has a weight average molecular weight of 5,000 to 2,000,000 Daltons (preferably, 10,000 to 1,500,000 Daltons; more preferably, 20,000 to 100,000 Daltons; most preferably, 20,000 to 50,000 Daltons) and wherein the weight ratio of the partially hydrolyzed poly (vinyl acetate) to the poly(vinyl pyrrolidone) in the free standing film is >10:1 (preferably, at least 100:1; more preferably, at least 150:1; most preferably, 150:1 to 600:1).

Preferably, the free standing film of the present invention, further comprises 0 to 10 wt % of an optional additive. More preferably, the free standing film of the present invention, further comprises 0 to 10 wt % of an optional additive; wherein the optional additive is selected from the group consisting of a preservative, an antioxidant, a viscosity modifier, a solubility modifier, an antimicrobial agent, a binder, a chelating, a filler, an extender, a defoamer, a lubricant, a release agent, an anti-blocking agent, a tackifier, a coalescent, a detackifying agent and a nanoparticle (e.g., silicate type nanoclay).

Preferably, the free standing film of the present invention, further comprises 0 to 10 wt % of an optional additive, wherein the optional additive includes a nanoparticle (preferably, a silicate type nanoclay). More preferably, the free standing film of the present invention, further comprises 0.05 to 1 wt % (more preferably, 0.1 to 0.5 wt %; most preferably, 0.1 to 0.3 wt %) of a nanoparticle (preferably, a silicate type nanoclay). Most preferably, the free standing film of the present invention, comprises 0.1 to 0.3 wt % of a nanoparticle (preferably, a silicate type nanoclay).

Preferably, the free standing film of the present invention, further comprises 0 to 10 wt % of an optional additive, wherein the optional additive includes a defoamer. More preferably, the free standing film of the present invention, further comprises 1 to 10 wt % (more preferably, 2 to 7.5 wt %; most preferably, 3 to 6 wt %) of an defoamer. Most preferably, the free standing film of the present invention comprises 3 to 6 wt % of a defoamer.

The water soluble films of the present invention can be prepared by techniques known to those skilled in the art including, for example, via solution casting on a substrate, such as glass, polyethylene terephthalate (PET) or metal. Typically, water is used as the solvent for the solution casting, although other solvents may be used. Following casting, the films may be dried by heating at elevated temperature, for instance 65-80° C.

The free standing film of the present invention has utility as a water soluble (preferably, cold water soluble) packaging film that facilitates dosing of materials, for example, a premeasured unit dose of a household care composition, such as, a hard surface cleaning formulation, a dish care formulation, rinse aid formulation for automatic dishwashing, a laundry detergent formulation or fabric conditioner formulation. Preferably, the free standing film of the present invention forms a cavity. More preferably, the free standing film of the present invention forms a cavity, wherein the cavity is encapsulated by the free standing film.

Preferably, the unit dose detergent package of the present invention, comprises: a free standing film of the present invention; and a detergent formulation. More preferably, the unit dose detergent package of the present invention, comprises: a free standing film of the present invention; and a detergent formulation; wherein the free standing film forms a cavity; wherein the detergent formulation is disposed within the cavity; and wherein the detergent formulation is in contact with the free standing film. Still more preferably, the unit dose detergent package of the present invention, comprises: a free standing film of the present invention; and a detergent formulation; wherein the free standing film forms a cavity; wherein the detergent formulation is disposed within the cavity; wherein the free standing film encapsulates the cavity; and wherein the detergent formulation is in contact with the free standing film. Most preferably, the unit dose detergent package of the present invention, comprises: a free standing film of the present invention; and a detergent formulation, comprising 10 to 60 wt %, based on weight of the detergent formulation, of a surfactant (preferably, wherein the surfactant is selected from the group consisting of cationic surfactants, anionic surfactants, nonionic surfactants, zwitterionic surfactants and mixtures thereof; more preferably, wherein the surfactant includes a nonionic surfactant); wherein the free standing film forms a cavity; wherein the detergent formulation is disposed within the cavity; wherein the free standing film encapsulates the cavity; and wherein the detergent formulation is in contact with the free standing film.

Preferably, the unit dose detergent package of the present invention comprises a free standing film of the present and a detergent formulation; wherein the free standing film forms a sealed container containing the detergent formulation. The sealed container can be formed by any suitable method, including such processes and features as heat sealing, solvent welding, and adhesive sealing solution (e.g., with use of a water-soluble adhesive).

Preferably, the detergent formulation used in the unit dose detergent package of the present invention, further comprises an optional component selected from the group consisting of a preservative, an antioxidant, a viscosity modifier, a solubility modifier, an antimicrobial agent, a binder, a chelating agent, a fungicide, an aesthetics enhancer and a filler.

Preferably, the unit dose detergent package of the present invention, comprises: a free standing film of the present invention; and a detergent formulation; wherein the detergent formulation is a hard surface cleaning concentrate. More preferably, the unit dose detergent package of the present invention, comprises: a free standing film of the present invention; and a hard surface cleaning concentrate; wherein the hard surface cleaning concentrate, comprises: a glycol ether of formula I (preferably, 15 to 50 wt % (more preferably, 20 to 40 wt %; still more preferably, 25 to 30 wt %; most preferably, 26 to 28 wt %), based on weight of the hard surface cleaning concentrate, of the glycol ether of formula I)

(I)

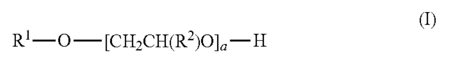

wherein $R^1$ is a linear or branched $C_{2-8}$ alkyl group; wherein each $R^2$ is independently selected from the group consisting of a hydrogen and a methyl group; and wherein a is 1 to 3; a nonionic surfactant of formula II (preferably, 10 to 60 wt % (more preferably, 25 to 50 wt %; still more preferably, 30 to 40 wt %; most preferably, 34 to 38 wt %), based on weight of the hard surface cleaning concentrate, of the nonionic surfactant of formula II)

(II)

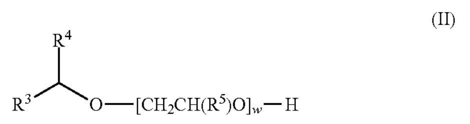

wherein w is an average of 5 to 40 (preferably, 7 to 27; more preferably, 8 to 20; most preferably, 7 to 12); wherein $R^3$ is selected from the group consisting of a hydrogen and a linear or branched $C_{1-20}$ alkyl group; wherein $R^4$ is a linear or branched $C_{1-20}$ alkyl group; and wherein each $R^5$ is independently selected from the group consisting of a hydrogen, a methyl group, an ethyl group, a n-propyl group, an iso-propyl group, a n-butyl group, a 2-butyl group and a 2-methyl-2-butyl group (preferably, a hydrogen, a methyl group and an ethyl group; more preferably, a hydrogen and a methyl group; most preferably, a hydrogen); with the proviso that sum of the total number of carbon atoms in $R^3$ and $R^4$ is 5 to 21; and a tertiary amine (preferably, 15 to 60 wt % (more preferably, 20 to 50 wt %; still more preferably, 25 to 40 wt %; most preferably, 27 to 34 wt %), based on weight of the hard surface cleaning concentrate, of the tertiary amine) (preferably, wherein the tertiary amine is of formula III

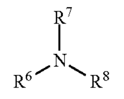

wherein $R^6$, $R^7$ and $R^8$ are independently selected from a linear or branched $C_{1-20}$ alkyl group and a linear or branched $C_{1-20}$ hydroxyalkyl group (preferably; a linear or branched $C_{1-10}$ alkyl group and a linear or branched $C_{1-10}$ hydroxyalkyl group; more preferably, a branched $C_{3-5}$ alkyl group or a branched $C_{3-5}$ hydroxyalkyl group; most preferably, a branched $C_3$ hydroxyalkyl group); wherein the water soluble film encapsulates the concentrated hard surface cleaning composition.

Preferably, the unit dose detergent package of the present invention, comprises: a hard surface cleaning concentrate, comprising: 15 to 50 wt % (preferably, 20 to 40 wt %; more preferably, 25 to 30 wt %; most preferably, 26 to 28 wt %), based on weight of the hard surface cleaning concentrate, of a glycol ether of formula I

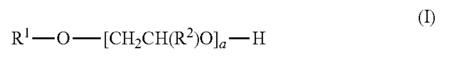

(I)

wherein $R^1$ is a linear or branched $C_{2-8}$ alkyl group (preferably, a linear or branched $C_{3-8}$ alkyl group; more preferably, a linear $C_{4-7}$ alkyl group; most preferably, a linear $C_6$ alkyl group); wherein each $R^2$ is independently selected from the group consisting of a hydrogen and a methyl group (preferably, wherein each $R^2$ is a hydrogen); and wherein a is 1 to 3 (preferably, wherein a is 2). More preferably, the unit dose detergent package of the present invention, comprises: a hard surface cleaning concentrate, comprising: 15 to 50 wt % (preferably, 20 to 40 wt %; more preferably, 25 to 30 wt %; most preferably, 26 to 28 wt %), based on weight of the hard surface cleaning concentrate, of a glycol ether of formula I; wherein $R^1$ is a linear $C_{4-7}$ alkyl group and wherein a is 2. Most preferably, the unit dose detergent package of the present invention, comprises: a hard surface cleaning concentrate, comprising: 15 to 50 wt % (preferably, 20 to 40 wt %; more preferably, 25 to 30 wt %; most preferably, 26 to 28 wt %), based on weight of the hard surface cleaning concentrate, of a glycol ether of formula I; wherein $R^1$ is a linear $C_6$ alkyl group and wherein a is 2.

Preferably, the unit dose detergent package of the present invention, comprises: a hard surface cleaning concentrate, comprising: 15 to 50 wt % (preferably, 20 to 40 wt %; more preferably, 25 to 30 wt %; most preferably, 26 to 28 wt %), based on weight of the hard surface cleaning concentrate, of a glycol ether of formula I, wherein the glycol ether of formula I is of formula Ia

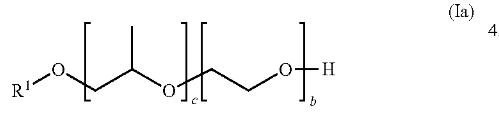

(Ia)

wherein $R^1$ is a linear or branched $C_{2-8}$ alkyl group (preferably, a linear or branched $C_{3-8}$ alkyl group; more preferably, a linear $C_{4-7}$ alkyl group; most preferably, a linear $C_6$ alkyl group); wherein b is an average of 0 to 3 (preferably, 0 to 2; more preferably 2); wherein c is an average of 0 to 3 (preferably, 0 to 2; more preferably 0); and with the proviso that b+c is an average of 1 to 3 (preferably, 2 to 3; more preferably, 2). More preferably, the unit dose detergent package of the present invention, comprises: a hard surface cleaning concentrate, comprising: 15 to 50 wt % (preferably, 20 to 40 wt %; more preferably, 25 to 30 wt %; most preferably, 26 to 28 wt %), based on weight of the hard surface cleaning concentrate, of a glycol ether of formula Ia; wherein $R^1$ is a linear $C_{4-7}$ alkyl group; wherein b is 2; and wherein c is 0. Most preferably, the unit dose detergent package of the present invention, comprises: a hard surface cleaning concentrate, comprising: 15 to 50 wt % (preferably, 20 to 40 wt %; more preferably, 25 to 30 wt %; most preferably, 26 to 28 wt %), based on weight of the hard surface cleaning concentrate, of a glycol ether of formula Ia; wherein $R^1$ is a linear $C_6$ alkyl group; wherein b is 2; and wherein c is 0.

Preferably, the unit dose detergent package of the present invention, comprises: a hard surface cleaning concentrate, comprising: 10 to 60 wt % (preferably, 25 to 50 wt %; more preferably, 30 to 40 wt %; most preferably, 34 to 38 wt %) (35 wt %; 36 wt %), based on weight of the hard surface cleaning concentrate, of a nonioinic surfactant of formula II

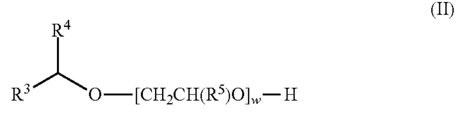

(II)

wherein w is an average of 5 to 40 (preferably, 7 to 27; more preferably, 8 to 20; most preferably, 7 to 12); wherein $R^3$ is selected from the group consisting of a hydrogen and a linear or branched $C_{1-20}$ alkyl group (preferably, a hydrogen, and a linear or branched $C_{1-15}$ alkyl group; more preferably, a hydrogen and a linear $C_{1-15}$ alkyl group); wherein $R^4$ is a linear or branched $C_{1-20}$ alkyl group (preferably, a linear or branched $C_{1-15}$ alkyl group; more preferably, a linear $C_{1-15}$ alkyl group); wherein each $R^5$ is independently selected from the group consisting of a hydrogen, a methyl group, an ethyl group, a n-propyl group, an iso-propyl group, a n-butyl group, a 2-butyl group and a 2-methyl-2-butyl group (preferably, a hydrogen, a methyl group and an ethyl group; more preferably, a hydrogen and a methyl group; most preferably, a hydrogen); and with the proviso that sum of the total number of carbon atoms in $R^3$ and $R^4$ is 5 to 21 (preferably, 6 to 20 carbon atoms; more preferably, 7 to 18 carbon atoms; most preferably, 11 to 15 carbon atoms). More preferably, the unit dose detergent package of the present invention, comprises: a hard surface cleaning concentrate, comprising: 20 to 60 wt % (preferably, 25 to 50 wt %; more preferably, 30 to 40 wt %; most preferably, 34 to 38 wt %) (35 wt %; 36 wt %), based on weight of the hard surface cleaning concentrate, of a nonionic surfactant of formula II; wherein w is an average of 8 to 16; wherein $R^3$ is selected from the group consisting of a hydrogen and a linear $C_{1-15}$ alkyl group; wherein $R^4$ is a linear or branched $C_{1-15}$ alkyl group; and with the proviso that the sum of the total number of carbon atoms in $R^3$ and $R^4$ is 6 to 20. Most preferably, the unit dose detergent package of the present invention, comprises: a hard surface cleaning concentrate, comprising: 20 to 60 wt % (preferably, 25 to 50 wt %; more preferably, 30 to 40 wt %; most preferably, 34 to 38 wt %) (35 wt %; 36 wt %), based on weight of the hard surface cleaning concentrate, of a nonioinic surfactant of formula II; wherein w is an average of 7 to 12; wherein $R^3$ is selected from the group consisting of a hydrogen and a linear $C_{1-15}$ alkyl group; wherein $R^4$ is a linear $C_{1-15}$ alkyl group; and with the proviso that the sum of the total number of carbon atoms in $R^3$ and $R^4$ is 7 to 18.

Preferably, the unit dose detergent package of the present invention, comprises: a hard surface cleaning concentrate, comprising: 20 to 60 wt % (preferably, 25 to 50 wt %; more preferably, 30 to 40 wt %; most preferably, 34 to 38 wt %), based on weight of the hard surface cleaning concentrate, of a nonioinic surfactant of formula II, wherein the nonionic surfactant of formula II is of formula IIa (IIa)

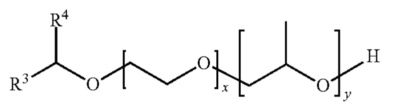

wherein x is an average of 5 to 15 (preferably, 7 to 12; more preferably, 8 to 10); wherein y is an average of 0 to 15 (preferably, 0 to 10; more preferably, 0 to 8; most preferably, 0 to 6); wherein $R^3$ is selected from the group consisting of a hydrogen and a linear or branched $C_{1-20}$ alkyl group (preferably, a hydrogen and a linear or branched $C_{1-15}$ alkyl group; more preferably, a hydrogen and a linear $C_{1-15}$ alkyl group); wherein $R^4$ is a linear or branched $C_{1-20}$ alkyl group (preferably, a linear or branched $C_{1-15}$ alkyl group; more preferably, a linear $C_{1-15}$ alkyl group); and with the proviso that the sum of the total number of carbon atoms in $R^3$ and $R^4$ is 5 to 21 (preferably, 6 to 20 carbon atoms; more preferably, 7 to 18 carbon atoms; most preferably, 11 to 15 carbon atoms). More preferably, the unit dose detergent package of the present invention, comprises: a hard surface cleaning concentrate, comprising: 20 to 60 wt % (preferably, 25 to 50 wt %; more preferably, 30 to 40 wt %; most preferably, 34 to 38 wt %), based on weight of the hard surface cleaning concentrate, of a nonioinic surfactant of formula IIa; wherein x is an average of 8 to 10; wherein y is an average of 0 to 6; wherein $R^3$ is selected from the group consisting of a hydrogen and a linear $C_{1-15}$ alkyl group; wherein $R^4$ is a linear or branched $C_{1-15}$ alkyl group; and with the proviso that the sum of the total number of carbon atoms in $R^3$ and $R^4$ is 6 to 20. Most preferably, the unit dose package of the present invention, comprises: a hard surface cleaning concentrate, comprising: 20 to 60 wt % (preferably, 25 to 50 wt %; more preferably, 30 to 40 wt %; most preferably, 34 to 38 wt %), based on weight of the hard surface cleaning concentrate, of a nonioinic surfactant of formula IIa; wherein x is an average of 7 to 12; wherein y is 0; wherein $R^3$ is selected from the group consisting of a hydrogen or a linear $C_{1-15}$ alkyl group; wherein $R^4$ is a linear $C_{1-15}$ alkyl group; and with the proviso that the sum of the total number of carbon atoms in $R^3$ and $R^4$ is 7 to 18.

Preferably, the unit dose detergent package of the present invention, comprises: a hard surface cleaning concentrate, comprising: 15 to 60 wt % (preferably, 20 to 50 wt %; more preferably, 25 to 40 wt %; most preferably, 27 to 34 wt %), based on weight of the hard surface cleaning concentrate, of a tertiary amine. More preferably, the unit dose detergent package of the present invention, comprises: a hard surface cleaning concentrate, comprising: 15 to 60 wt % (preferably, 20 to 50 wt %; more preferably, 25 to 40 wt %; most preferably, 27 to 34 wt %), based on weight of the hard surface cleaning concentrate, of a tertiary amine; wherein the tertiary amine is according to formula III

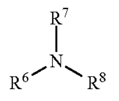

wherein $R^6$, $R^7$ and $R^8$ are independently selected from a linear or branched $C_{1-20}$ alkyl group (preferably; a linear or branched $C_{1-10}$ alkyl group and a linear or branched $C_{1-10}$ hydroxyalkyl group; more preferably, a branched $C_{3-5}$ alkyl group or a branched $C_{3-5}$ hydroxyalkyl group; most preferably, a branched $C_3$ hydroxyalkyl group). Still more preferably, the unit dose detergent package of the present invention, comprises: a hard surface cleaning concentrate, comprising: 15 to 60 wt % (preferably, 20 to 50 wt %; more preferably, 25 to 40 wt %; most preferably, 27 to 34 wt %), based on weight of the hard surface cleaning concentrate, of a tertiary amine of formula III; wherein $R^6$, $R^7$ and $R^8$ are independently selected from the group consisting of a linear or branched $C_{1-10}$ alkyl group and a linear or branched $C_{1-10}$ hydroxyalkyl group. Yet more preferably, the unit dose detergent package of the present invention, comprises: a hard surface cleaning concentrate, comprising: 15 to 60 wt % (preferably, 20 to 50 wt %; more preferably, 25 to 40 wt %; most preferably, 27 to 34 wt %), based on weight of the hard surface cleaning concentrate, of a tertiary amine of formula III; wherein $R^6$, $R^7$ and $R^8$ are independently selected from the group consisting of a branched $C_{3-5}$ alkyl group and a branched $C_{3-5}$ hydroxyalkyl group. Most preferably, the unit dose detergent package of the present invention, comprises: a hard surface cleaning concentrate, comprising: 15 to 60 wt % (preferably, 20 to 50 wt %; more preferably, 25 to 40 wt %; most preferably, 27 to 34 wt %), based on weight of the hard surface cleaning concentrate, of a tertiary amine of formula III; wherein $R^6$, $R^7$ and $R^8$ are a branched $C_3$ hydroxyalkyl group.

Preferably, the unit dose detergent package of the present invention, comprises a hard surface cleaning concentrate; wherein the hard surface cleaning concentrate optionally further comprises optional ingredient. Preferably, the hard surface cleaning concentrate, further comprises an optional ingredient; wherein the optional ingredient is selected from the group consisting of a salt, an enzyme, a corrosion inhibitor, an acid, a bleaching agent, an abrasive, an anti-microbial agent (e.g., phenoxyethanol, benzalkonium chloride), a rheology modifier, a film former (e.g., Acusol™ Pro), a pH adjuster, a buffering agent, an aesthetic colorant, a fragrance and mixtures thereof.

Preferably, the hard surface cleaning concentrate has a pH of ≤11. More preferably, the hard surface cleaning concentrate has a pH of 5 to 10.5. Most preferably, the hard surface cleaning concentrate has a pH of 8 to 10.

Preferably, the hard surface cleaning concentrate contains 0 to 10 wt % (preferably, 0 to 5 wt %; more preferably, 0 to 2.5 wt %; still more preferably, 0 to 2 wt %; yet more preferably, 0 to 1.5 wt %; most preferably, 0 to 1 wt %), based on weight of the hard surface cleaning concentrate, of water.

Preferably, the hard surface cleaning concentrate of the present invention contains<0.01 wt % (preferably, <0.001 wt %; more preferably, <0.0001 wt %; still more preferably, <0.0001 wt %; most preferably, less than the detectable limit), based on weight of the hard surface cleaning concentrate, of dispersant polymer. More preferably, the hard surface cleaning concentrate contains<0.01 wt % (preferably, <0.001 wt %; more preferably, <0.0001 wt %; still more preferably, <0.0001 wt %; most preferably, less than the detectable limit), based on weight of the hard surface cleaning concentrate, of dispersant polymer; wherein the dispersant polymer is selected from the group consisting of poly(acrylic acid), poly(acrylic acid/maleic acid) copolymers, poly(maleic acid/olefin) copolymers, phosphino carboxylated polymers and mixtures thereof.

Preferably, the hard surface cleaning concentrate contains<0.01 wt % (preferably, <0.001 wt %; more preferably, <0.0001 wt %; still more preferably, <0.0001 wt %; most preferably, less than the detectable limit), based on weight of the hard surface cleaning concentrate, of quaternary ammonium compounds.

Preferably, the hard surface cleaning concentrate contains<0.01 wt % (preferably, <0.001 wt %; more preferably, <0.0001 wt %; still more preferably, <0.0001 wt %; most preferably, less than the detectable limit), based on weight of the hard surface cleaning concentrate, of hydrotrope. More preferably, the hard surface cleaning concentrate contains<0.01 wt % (preferably, <0.001 wt %; more preferably, <0.0001 wt %; still more preferably, <0.0001 wt %; most preferably, less than the detectable limit), based on weight of the hard surface cleaning concentrate, of hydrotrope; wherein the hydrotrope is selected from the group consisting of calcium, sodium, potassium, ammonium and alkanol ammonium salts of xylene sulfonic acid; calcium, sodium, potassium, ammonium and alkanol ammonium salts of toluene sulfonic acid; calcium, sodium, potassium, ammonium and alkanol ammonium salts of ethylbenzene sulfonic acid; calcium, sodium, potassium, ammonium and alkanol ammonium salts of cumene sulfonic acid; and mixtures thereof.

Some embodiments of the present invention will now be described in detail in the following Examples.

Synthesis S1: Crosslinked Cellulose Ether

The crosslinking agent used in Synthesis S1 was a linear poly(propyleneglycol) diglycidyl ether made from polypropylene glycol (PPG) having a molecular weight of ~400 Daltons and having the formula

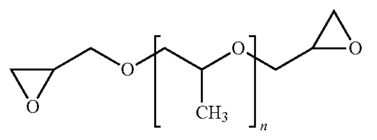

wherein n is 5.7 to 6.7 (available from Leuna-Harze GmbH, Leuna, DE as EPILOX™ M985 poly(propyleneglycol) diglycidylether crosslinker).

Ground cellulose flock (1.5 mol) was added to a 5 L autoclave. After purging the autoclave trice with nitrogen gas, the contents of the autoclave were heated to 40° C. Then dimethylether (DME, 4.7 mol/mol of anhydroglucose units (AGU)) and methyl chloride (MC1; 3.2 mol/mol AGU) were injected into the autoclave. Caustic soda (NaOH, strength 50 wt % aqueous, 1.9 mol NaOH/mol AGU) was added to the autoclave in 3 portions during 2 minutes at a temperature of 40° C. The reaction mixture was held at 40° C. for 30 minutes. Ethylene oxide (0.45 mol/mol AGU) was then added and the reaction mixture was held for 10 minutes at 40° C. The crosslinker (EPILOX™ M985 crosslinker; 0.0025 mol/mol AGU) was dissolved in 20 mL of isopropanol and added to the contents of the autoclave in six increments in 30 second intervals. The contents of the autoclave were then heated to 80° C. in 40 minutes. At 80° C. a water soluble monovalent copper ligand (MCL 2; 1.3 mol/mol AGU) was injected into the autoclave quickly. Afterwards, NaOH (0.67 mol/mol AGU) was added in 7 portions over 30 minutes, followed by a 70 minute cook-off time at 80° C. Following this, the product crosslinked cellulose ether was washed in hot (>95° C.) water, neutralized with formic acid, granulated, dried and milled.

Comparative Examples C1-C18 and Examples 1-15: Film/Additive Blends

Water soluble film/additive blends were prepared according to Comparative Examples C1-C18 and Examples 1-15 by mixing together the components in the concentrations noted in TABLE 1.

TABLE 1

| | Ingredient (wt %) | | | | | |
|---|---|---|---|---|---|---|
| | Water soluble film | | | Additive | | |
| Example | A | B | C | Description | (wt %) | Water |
| C1 | 1 | — | — | — | — | 99 |
| C2 | — | 1 | — | — | — | 99 |
| C3 | — | — | 1 | — | — | 99 |
| C4 | — | — | 0.9 | D | 0.1 | 99 |
| C5 | — | — | 0.75 | D | 0.25 | 99 |
| C6 | — | — | 0.5 | D | 0.5 | 99 |
| C7 | — | — | 0.25 | D | 0.75 | 99 |
| C8 | — | — | 0.1 | D | 0.9 | 99 |
| C9 | — | — | 0.9 | E | 0.1 | 99 |
| C10 | — | — | 0.75 | E | 0.25 | 99 |
| C11 | — | — | 0.5 | E | 0.5 | 99 |
| C12 | — | — | 0.25 | E | 0.75 | 99 |
| C13 | — | — | 0.1 | E | 0.9 | 99 |
| C14 | — | — | 0.9 | F | 0.1 | 99 |
| C15 | — | — | 0.75 | F | 0.25 | 99 |
| C16 | — | — | 0.5 | F | 0.5 | 99 |
| C17 | — | — | 0.25 | F | 0.75 | 99 |
| C18 | — | — | 0.1 | F | 0.9 | 99 |
| 1 | 0.9 | — | — | G | 0.1 | 99 |
| 2 | 0.75 | — | — | G | 0.25 | 99 |
| 3 | 0.5 | — | — | G | 0.5 | 99 |
| 4 | 0.25 | — | — | G | 0.75 | 99 |
| 5 | 0.1 | — | — | G | 0.9 | 99 |
| 6 | — | 0.9 | — | G | 0.1 | 99 |
| 7 | — | 0.75 | — | G | 0.25 | 99 |
| 8 | — | 0.5 | — | G | 0.5 | 99 |
| 9 | — | 0.25 | — | G | 0.75 | 99 |
| 10 | — | 0.1 | — | G | 0.9 | 99 |
| 11 | — | — | 0.9 | G | 0.1 | 99 |
| 12 | — | — | 0.75 | G | 0.25 | 99 |
| 13 | — | — | 0.5 | G | 0.5 | 99 |
| 14 | — | — | 0.25 | G | 0.75 | 99 |
| 15 | — | — | 0.1 | G | 0.9 | 99 |

A MonoSol M8312 polyvinyl alcohol based film from MonoSol LLC
B Solublon GA-BTX 75 μm polyvinyl alcohol based film from Aicello Corporation
C Solublon GA-BTX 90 μm polyvinyl alcohol based film from Aicello Corporation
D SUPRACARE ™ 760 additive from The Dow Chemical Company
E CELLOSIZE ™ QP 100 MH from The Dow Chemical Company
F CELLOSIZE ™ Texture 40-0202 from The Dow Chemical Company
G Product of Synthesis S1

Viscosity Measures of Film Blended with Additive

The viscosity of the water soluble film/additive blends prepared according to Comparative Examples C1-C18 and Examples 1-15 were measured using a Brookfield DV-II programmable viscometer with a CP-52 spindle at 25° C. Measurements were taken at 5 rpm, 10 rpm, 20 rpm and 50 rpm for each blend and are reported in TABLE 2.

TABLE 2

| | Viscosity (cP) | | | |
|---|---|---|---|---|
| Example | 5 rpm | 10 rpm | 20 rmp | 50 rpm |
| C1 | 1 | 1 | 1 | 1 |
| C2 | 1 | 1 | 1 | 1 |
| C3 | 1 | 1 | 1 | 1 |
| C4 | 1 | 1 | 1 | 1 |
| C5 | 1 | 20 | 20 | 20 |
| C6 | 238 | 260 | 200 | 130 |
| C7 | 1,110 | 800 | 580 | 350 |
| C8 | 2,000 | 1,380 | 930 | 530 |
| C9 | 40 | 40 | 5 | 16 |
| C10 | 60 | 40 | 40 | 32 |
| C11 | 280 | 250 | 170 | 120 |
| C12 | 890 | 650 | 470 | 280 |
| C13 | 1,630 | 1,120 | 750 | 430 |
| C14 | 40 | 30 | 5 | 10 |

TABLE 2-continued

| Example | Viscosity (cP) 5 rpm | 10 rpm | 20 rmp | 50 rpm |
|---|---|---|---|---|
| C15 | 140 | 70 | 20 | 15 |
| C16 | 100 | 70 | 20 | 50 |
| C17 | 180 | 130 | 100 | 80 |
| C18 | 240 | 190 | 150 | 120 |
| 1 | 1 | 1 | 5 | 6 |
| 2 | 40 | 40 | 40 | 32 |
| 3 | 540 | 370 | 260 | 160 |
| 4 | 1,700 | 1,130 | 740 | 410 |
| 5 | 2,860 | 1,830 | 1,170 | 620 |
| 6 | 1 | 1 | 1 | 2 |
| 7 | 60 | 40 | 30 | 26 |
| 8 | 220 | 210 | 160 | 105 |
| 9 | 730 | 580 | 450 | 290 |
| 10 | 1,530 | 1,040 | 810 | 500 |
| 11 | 1 | 1 | 5 | 6 |
| 12 | 60 | 50 | 45 | 35 |
| 13 | 400 | 310 | 230 | 150 |
| 14 | 1,230 | 870 | 610 | 370 |
| 15 | 2,460 | 1,700 | 1,130 | 640 |

Examples 16-25: Water Soluble Film

Water soluble films were formed in each of Examples 16-25 by placing a water soluble film/additive blend prepared according to one of Examples 1-10, as noted in TABLE 3, in a vented oven at 60° C. and drying to form the film. Once formed, the films were then redispersed in water forming a 1 wt % solution in water. The viscosity of these 1 wt % solutions were then measured using a Brookfield DV-II programmable viscometer with a CP-52 spindle at 25° C. Measurements were taken at 5 rpm, 10 rpm, 20 rpm and 50 rpm for each blend and are reported in TABLE 3.

TABLE 3

| Example | Starting Blend | Viscosity (cP) 5 rpm | 10 rpm | 20 rmp | 50 rpm |
|---|---|---|---|---|---|
| 16 | Example 1 | 1 | 1 | 1 | 2 |
| 17 | Example 2 | 120 | 120 | 100 | 75 |
| 18 | Example 3 | 400 | 320 | 240 | 150 |
| 19 | Example 4 | 3,400 | 2,230 | 1,420 | 760 |
| 20 | Example 5 | 4,500 | 2,900 | 1,840 | 950 |
| 21 | Example 6 | 1 | 1 | 1 | 1 |
| 22 | Example 7 | 60 | 40 | 30 | 20 |
| 23 | Example 8 | 200 | 150 | 105 | 80 |
| 24 | Example 9 | 520 | 400 | 340 | 220 |
| 25 | Example 10 | 900 | 610 | 500 | 340 |

Synthesis S2: Concentrated Hard Surface Cleaning Composition

Concentrated hard surface cleaning composition of Synthesis S2 was prepared by mixing together the components in the weight proportions noted in TABLE 4.

TABLE 4

| Component | wt % |
|---|---|
| Biodegradable, seconday alcohol ethoxylate[1] | 35.0 |
| Triisopropyl amine[2] | 34.0 |
| Hexyl Carbitol | 19.5 |
| Glycol ether[3] | 5.0 |
| Benzoalkonium chloride | 2.5 |

TABLE 4-continued

| Component | wt % |
|---|---|
| Fragrance[4] | 3.0 |
| Yellow dye[5] | 0.9 |
| Red dye[6] | 0.1 |

[1]TERGITOL ™ 15-S-9 from The Dow Chemical Company
[2]TIPA LFT 85 from The Dow Chemical Company
[3]DOWANOL ™ EPH from The Dow Chemical Company
[4]Kool & Fresh available from Givaudan
[5]Liquitint Yellow EC available from Milliken Chemical
[6]Liquitint Red OC available from Milliken Chemical

Film Resistance to Concentrated Hard Surface Cleaning Composition

A drop of the concentrated hard surface cleaning composition prepared according to Synthesis S2 was applied to the surface of a water soluble films formed according to each of Examples 16-25. Each of the films were observed to resist penetration of the concentrated hard surface cleaning composition for a month.

Synthesis S3: Free Standing Film

Crosslinked cellulose ether prepared according to Synthesis S1 (1 g), calcium chloride dihydrate (0.4 g) and deionized water (98.6 g) were mixed together. The mixture was then deposited on a substrate and dried in a vented oven at 60° C. to form a film.

Free Standing Film Resistance to Concentrated Hard Surface Cleaning Composition Concentrated hard surface cleaning composition prepared according to Synthesis S2 (1 mL) was added to an Ependorf tube. The free standing film prepared according to Synthesis S3 was used to cap the opening of the Ependorf tube. The Ependorf tube was then turned over with the opening facing down so that the concentrated hard surface cleaning composition inside the tube was supported by the free standing film. The free standing film was observed to resist the concentrated hard surface cleaning composition for a month without penetration.

We claim:

1. A free standing film, comprising:

20 to 100 wt %, based on weight of the free standing film, of an irreversibly crosslinked cellulose ether containing 0.1 to 0.6 wt %, based on weight of the crosslinked cellulose ether, of polyether groups.

2. The free standing film of claim 1, wherein the free standing film has an average thickness of 5 to 200 μm.

3. The free standing film of claim 2, wherein the polyether groups in the irreversibly crosslinked cellulose ether are polyoxyalkylene groups having 2 to 100 oxyalkylene groups.

4. The free standing film of claim 3, wherein the polyoxyalkylene groups are selected from the group consisting of a polyoxyethylene, a polyoxypropylene and combinations thereof.

5. The free standing film of claim 4, wherein the irreversibly crosslinked cellulose ether comprises a base cellulose ether and crosslinks; wherein the crosslinks contain the polyether groups; and wherein the base cellulose ether contains hydroxyalkyl ether and alkyl ether groups.

6. The free standing film of claim 5, wherein the base cellulose ether is selected from the group consisting of hydroxyethyl methylcellulose, hydroxypropyl methyl cellulose, methyl hydroxyethyl hydroxypropylcellulose, ethyl hydroxyethyl cellulose and combinations thereof.

7. The free standing film of claim 6, further comprising at least one of:

(a) 5 to 80 wt %, based on weight of the free standing film, of a partially hydrolyzed poly(vinyl acetate);

(b) 0.1 to 45 wt %, based on weight of the free standing film, of a crosslinking agent;

(c) 0.1 to 45 wt %, based on weight of the free standing film, of a poly(ethylene oxide) having a weight average molecular weight of 20,000 to 2,000,000 Daltons;

(d) 0.1 to 35 wt %, based on weight of the free standing film, of a poly(alkylene glycol) having a weight average molecular weight of >400 to 5,300 Daltons;

(e) 0.1 to 45 wt %, based on weight of the free standing film, of a plasticizer;

(f) 0.1 to 10 wt %, based on weight of the free standing film, of a poly(isobutylene-co-maleic anhydride) copolymer, wherein the poly(isobutylene-co-maleic anhydride) copolymer is at least partially neutralized; and (g) 0.01 to 1.8 wt %, based on weight of the free standing film, of a poly(vinyl pyrrolidone).

8. The free standing film of claim 7, wherein the free standing film comprises:

20 to 95 wt %, based on weight of the free standing film, of the crosslinked cellulose ether containing 0.1 to 0.6 wt %, based on weight of the crosslinked cellulose ether, of polyether groups; and 5 to 80 wt %, based on weight of the free standing film, of the partially hydrolyzed poly(vinyl acetate).

9. The free standing film of claim 8, further comprising an optional additive; wherein the optional additive is selected from the group consisting of a preservative, an antioxidant, a viscosity modifier, a solubility modifier, an antimicrobial agent, a binder, a chelating agent, a filler, an extender, a defoamer, a lubricant, a release agent, an anti-blocking agent, a tackifier, a coalescent, a detackifying agent and a nanoparticle.

10. A unit dose detergent package, comprising:

a free standing film of claim 1; and a detergent formulation, comprising 10 to 60 wt %, based on weight of the detergent formulation, of a surfactant;

wherein the free standing film forms a cavity; wherein the detergent formulation is disposed within the cavity; wherein the detergent formulation is in contact with the free standing film; and wherein the free standing film encapsulates the detergent formulation.

* * * * *